United States Patent [19]
Sato et al.

[11] Patent Number: 5,732,117
[45] Date of Patent: Mar. 24, 1998

[54] METHOD OF PRODUCING INTERPOLATION DATA, METHOD OF INFERRING POSITION OF SHARP VARYING PLANE OF X-RAY ABSORPTION COEFFICIENTS, AND X-RAY COMPUTERIZED TOMOGRAPHY(CT) APPARATUS

[75] Inventors: Natsuko Sato; Makoto Gono, both of Tokyo, Japan

[73] Assignee: GE Yokogawa Medical Systems, Limited, Tokyo, Japan

[21] Appl. No.: 734,563

[22] Filed: Oct. 21, 1996

[51] Int. Cl.⁶ .................................................. A61B 6/03
[52] U.S. Cl. ........................................ 378/15; 378/901
[58] Field of Search ................................ 378/4, 15, 901

[56] References Cited

U.S. PATENT DOCUMENTS

| | | | |
|---|---|---|---|
| 5,073,911 | 12/1991 | Ozaki et al. | 378/17 |
| 5,241,576 | 8/1993 | Lann | 378/19 |
| 5,270,923 | 12/1993 | King et al. | 382/131 |
| 5,345,381 | 9/1994 | Wallschlaeger | 378/15 |
| 5,412,703 | 5/1995 | Goodenough | 378/8 |
| 5,544,212 | 8/1996 | Heuscher | 378/15 |

OTHER PUBLICATIONS

Multidimensional signal processing, audio and electroacoustics, Glasgow, May 23–6, 1989. vol. 3, May 23,1989, IEEE pp. 1472–1475.

*Primary Examiner*—David P. Porta
*Assistant Examiner*—David Vernon Bruce
*Attorney, Agent, or Firm*—Moonray Kojima

[57] ABSTRACT

A data processing technique for X-ray computerized tomography (CT) calculates the difference of two pieces of data having a same X-ray trajectory and existing on both sides of a plane of concern, and accumulates the differential value in a coordinate-correspondent buffer of respective xy coordinates on the X-ray trajectory. It repeats the operation for raw data of at least one turn on one side of the plane of concern, and stores the accumulative values in the buffers together with the z-axis position of the plane of concern. It repeats the operation while varying the z-axis position within a prescribed range on the plane of concern, and infers, based on the distribution along z-axis positions of the accumulative values in the buffers of same xy coordinates, the z-axis position of sharp varying plane of X-ray absorption coefficients relevant to the xy coordinates. It calculates weighting factors based on the relation between the slicing position, slice thickness and position of a sharp varying plane of X-ray absorption coefficients for interpolation data, calculates the interpolation data with the weighting factors, and reconstructs an image by using the interpolation data.

10 Claims, 15 Drawing Sheets

FIG.6

Start process of inferring the position of sharp varying plane of X-ray absorption coefficients.

V1 Set start position Ss and end position Se of inference.

V2 Repeat operation by shifting position Sm from Ss to Se.

V3 Repeat operation by shifting position Sk from Sm to position of 360°- advancement.

V4 Get difference d(nk,ik,j) of raw data R(nk,ik,j) at position Sk from raw data R(nk-1,ik,j) at position of 360° procedence.

V5 |d (nk,ik,j)| > $\alpha$ ?

V6 Get coordinates (x,y) located on X-ray trajectory T (ik,j) from sinogram, and add d (nk,ik,j) to buffer Bm (x,y) relevant to (x,y).

V7 Repeat operation for all coordinates (x,y).

V8 Find position Sp (x,y) at which accumulative value Dm (x,y) is greater than threshold value $\beta$ and is the peak of distribution along z - axis, thereby determining the (x,y) and Sp (x,y) to be the position of sharp varying plane of X-ray absorption coefficients.

End

METHOD OF PRODUCING INTERPOLATION DATA, METHOD OF INFERRING POSITION OF SHARP VARYING PLANE OF X-RAY ABSORPTION COEFFICIENTS, AND X-RAY COMPUTERIZED TOMOGRAPHY(CT) APPARATUS

BACKGROUND OF THE INVENTION

1. Field of the Invention

The present invention relates to a method of producing interpolation data, a method of inferring the position of a sharp varying plane of X-ray absorption coefficients, and an X-ray computerized tomography (CT) apparatus. More particularly, the invention relates to a method of producing interpolation data so that artifacts attributable to partial volume can be reduced, a method of inferring the position of a sharp varying plane of X-ray absorption coefficients, and an X-ray CT apparatus capable of carrying out these methods properly.

2. Description of the Prior Art

FIG. 1 is a flowchart showing a conventional sequential process for collecting image data based on helical scanning and producing an image from the data.

Step B1 samples raw data by helical scanning. Specifically, an X-ray tube and associated detector are turned around an object under test, while the object (or alternatively the X-ray tube and detector) is moved straight along an axis, i.e., z axis, and raw data of views at multiple sampling positions on the z axis is sampled. For a turn number n of the turning of X-ray tube and detector, a view number i, and a detector channel number j, a piece of raw data is expressed as $R(n,i,j)$.

Step B2 specifies an image reconstructing position So.

Step B4' samples data of all views at the position So needed for image reconstruction. Specifically, if raw data $R(no,io,j)$ at the position So exists, it is taken in, and furthermore data $to(ix,j)$ for view number ix other than io is calculated by interpolation from raw data $R(nx',ix,j)$ of a nearby view with a smaller turn number than that of So (will be called "on one side" of So) and raw data $R(nx'',ix,j)$ of another nearby view with a larger turn number than that of So (will be called "on another side" of So).

For example, referring to FIG. 2, when raw data $R(nx1',ix,j)$ nearest to the image reconstructing position So among raw data $R(nx',ix,j)$ on one side has position S1 and raw data $R(nx1'',ix,j)$ nearest to So among raw data $R(nx'',ix,j)$ on another side has position S2, interpolation data $to(ix,j)$ is given as follows.

$$ro(ix,j) = \zeta \cdot R(nx1',ix,j) + \eta \cdot R(nx1'',ix,j)$$

where $\zeta = |S2-So|/|S1-S2|$ and $\eta = |S1-So|/|S1-S2|$.

In FIG. 2, Fo represent the X-ray trajectories of raw data $R(no,io,1)$, $R(no,io,(j+1)/2)$, and $R(no,io,J)$, Fx represent the X-ray trajectories of raw data $R(no,ix,1)$, $R(no,ix,(J+1)/2)$, and $R(no,ix,J)$, and curve G represents the relation between the angle of X-ray trajectory of the detector with channel number $j=(J+1)/2$ and the z-axis position.

Step B5 converts the raw data $R(no,io,j)$ and interpolation data $to(ix,j)$ into projection data, and reconstructs an image at the position So from the projection data.

The step B4' occasionally calculates the interpolate data $to(ix,j)$ from raw data $R(nt',it',jt')$ of a nearby confronting view on one side of So and raw data $R(nt'',it'',jt'')$ of another nearby confronting view on another side.

The foregoing prior art scheme of the calculation of interpolation is described in Japanese patent Laid-open No. Hei-2-211129, for example.

FIG. 3 explains the positional relation of the slice thickness W1 for the raw data $R(nx1',ix,j)$ on one side, slice thickness W2 for the raw data $R(nx1'',ix,j)$ on another side and slice thickness W0 for the interpolation data $to(ix,j)$ and the sharp varying plane Pv of X-ray absorption coefficients which is the border between X-ray absorption coefficients $\mu0$ and $\mu1$ that are different significantly. The X-ray absorption coefficient $\mu0$ is of bone (with a CT value ranging from 800 to 3000) and $\mu1$ is of air (with a CT value of about $-1000$), for example.

In case a sharp varying plane Pv of X-ray absorption coefficients exists inside of the slice thicknesses W1 and W2 as shown in FIG. 3 (this state is called "partial volume"), the interpolation data $ro(ix,j)$ must be calculated in consideration of the fact that the raw data $R(nx1',ix,j)$ and $R(nx1'',ix,j)$ are affected by the different X-ray absorption coefficients $\mu0$ and $\mu1$.

However, the conventional interpolation data calculating scheme is merely based on the weighting in terms of the inverse proportion of the distances between the position So of interpolation data $to(ix,j)$ and the positions S1 and S2 of nearby raw data $R(nx',ix,j)$ and $R(nx'',ix,j)$, and does not consider the influence of the existence of different X-ray absorption coefficients $\mu0$ and $\mu1$, i.e., the influence of partial volume. On this account, the prior art is deficient in that line-shaped or band-shaped partial volume artifacts are liable to emerge. Partial volume artifacts are pronounced when the labyrinth where bone and air coexist is sliced, for example.

SUMMARY OF THE INVENTION

Accordingly, a first object of the invention is to provide a method of producing interpolation data capable of reducing partial volume artifacts.

A second object of the invention is to provide a method of inferring the position of a sharp varying plane of X-ray absorption coefficients.

A third object of the invention is to provide an X-ray CT apparatus capable of carrying out properly the method of producing interpolation data and the method of inferring the position of a sharp varying plane of X-ray absorption coefficients.

The invention based on a first viewpoint resides in a method of producing interpolation data, the method comprising the steps of collecting data while turning at least one of an X-ray tube and a detector around an object under test and providing a linear movement for the object relative to the X-ray tube and/or detector, evaluating weights which depend on the degree of influence of partial volume on data for the position of interpolation, and producing interpolation data for an image reconstruction plane from the collected data based on the computation of weighted interpolation with the weights.

The invention based on a second viewpoint resides in the above-mentioned method of producing interpolation data, wherein said method evaluates X-ray attenuation coefficients on both sides of a sharp varying plane of X-ray absorption coefficients from data used for producing interpolation data, calculates a mean X-ray attenuation coefficient by weight-averaging the X-ray attenuation coefficients with said weights, and calculates interpolation data by using the mean X-ray attenuation coefficient.

The invention based on a third viewpoint resides in a method of inferring the position of a sharp varying plane of X-ray absorption coefficients, the method comprising the steps of collecting data while turning at least one of an X-ray tube and a detector around an object under test and providing a linear movement for the object relative to the X-ray tube and/or detector, calculating the difference of two pieces of data having a same X-ray trajectory and existing on both sides of a plane of concern and adding the differential value to a coordinate-correspondent buffer of respective xy coordinates on the X-ray trajectory, with the operation being repeated for data of multiple views near the plane of concern, storing the accumulative values in the buffers together with the z-axis position of the plane of concern, with the operation being repeated while varying the z-axis position within a prescribed range on the plane of concern, obtaining the distribution along z-axis positions of the accumulative values in the buffers of same xy coordinates, and inferring the z-axis position of sharp varying plane of X-ray absorption coefficients for the xy coordinates based on the distribution.

The invention based on a fourth viewpoint resides in a method of inferring the position of a sharp varying plane of X-ray absorption coefficients, the method comprising the steps of sampling data at multiple z-axis positions along at least two directions of different angles of an X-ray tube or a detector relative to an object under test, adding the sampled data to coordinate-correspondent buffers of respective xy coordinates on the X-ray trajectories, obtaining the distribution along z-axis positions of the accumulative values in the buffers of same xy coordinates, and inferring the z-axis position of sharp varying plane of X-ray absorption coefficients for the xy coordinates based on the distribution.

The invention based on a fifth viewpoint resides in a method of inferring the position of a sharp varying plane of X-ray absorption coefficients, the method comprising the steps of sampling data at multiple z-axis positions along a same direction of an X-ray tube or a detector relative to an object under test, storing sampled data of respective detector channels at respective z-axis positions in channel-correspondent buffers of respective detector channels, obtaining the distribution along z-axis positions of the contents of the buffers of a same detector channel, inferring the z-axis position of sharp varying plane of X-ray absorption coefficients for respective detector channels based on the distribution, storing data of the inferred z-axis positions in coordinate-correspondent buffers of respective xy coordinates on the X-ray trajectories, sampling data at the inferred z-axis positions along at least one direction of the X-ray tube or detector different from the first-mentioned angle, adding the sampled data to the coordinate-correspondent buffers of respective xy coordinates on the X-ray trajectories, and inferring the xy-coordinate position of sharp varying plane of X-ray absorption coefficients for the inferred z-axis position based on the accumulated values in the coordinate-correspondent buffers.

The invention based on a sixth viewpoint resides in an X-ray CT apparatus which comprises means for collecting data while turning at least one of an X-ray tube and a detector around an object under test and providing a linear movement for the object relative to the X-ray tube and/or detector, means for calculating weighting factors that depend on the degree of the influence of partial volume on data at the position of interpolation, means for implementing the computation of weighted interpolation with the calculated weighting factors for the data collected by the data collecting means, and means for reconstructing an image on an image reconstruction plane by implementing the image reconstructing computation by using the interpolation data resulting from the interpolation by the interpolation computing means.

The invention based on a seventh viewpoint resides in the above-mentioned X-ray CT apparatus, wherein the weighting factor calculating means calculates weighting factors based on the relation between the z-axis position of interpolation data, slice thickness and z-axis position of sharp varying plane of X-ray absorption coefficients.

The invention based on an eighth viewpoint resides in the above-mentioned X-ray CT apparatus, wherein the weighted interpolation computing means calculates X-ray attenuation coefficients on both sides of the sharp varying plane of X-ray absorption coefficients based on data used for producing interpolation data, evaluates a mean X-ray attenuation coefficient by calculating a weighted mean of X-ray attenuation coefficients with the weighting factors, and calculates interpolation data by using the mean X-ray attenuation coefficient.

In the interpolation data producing method of the first viewpoint, interpolation data on an image reconstruction plane is produced from data sampled by helical scanning based on the computation of weighted interpolation with weights that depend on the degree of the influence of partial volume on the interpolation data. Consequently, partial volume artifacts can be reduced.

In the interpolation data producing method of the second viewpoint, X-ray attenuation coefficients on one and another sides of the position of a sharp varying plane of X-ray absorption coefficients are evaluated from data used for producing interpolation data. Next, a weighted mean of the X-ray attenuation coefficients is calculated by using the above-mentioned weights. Next, interpolation data is calculated by using the mean X-ray attenuation coefficient. In consequence, the method renders the weighting to projection data, as will be explained in detail later, enabling information of smaller X-ray absorption coefficients to contribute significantly to the image.

In the method of inferring the position of a sharp varying plane of X-ray absorption coefficients of the third viewpoint, the difference of two pieces of data having a same X-ray trajectory and existing on both sides of a plane of concern is calculated and the differential value is accumulated in a coordinate-correspondent buffer of respective xy coordinates, the operation being repeated for data of multiple views near the plane of concern, the accumulative values in the buffers are stored together with the z-axis position of the plane of concern. The operation is repeated while varying the z-axis position within a certain range on the plane of concern. Based on the distribution of accumulative values in the coordinate-correspondent buffers of the same xy coordinates along the z-axis positions on the plane of concern, the z-axis position of sharp varying plane of X-ray absorption coefficients for the xy coordinates is inferred.

The differential value is greater if the sharp varying plane of X-ray absorption coefficients is located between two pieces of data. Accordingly, in adding data to coordinate-correspondent buffers, the nearer the plane of concern to the sharp varying plane of X-ray absorption coefficients, the larger is the number of times of addition of larger differential values and thus the larger is value of buffer contents. The value of buffer contents is maximum when the plane of concern coincides with the sharp varying plane of X-ray absorption coefficients. Accordingly, based on the distribution of accumulative values along z-axis positions in the coordinate-correspondent buffers for the same xy coordinates, the peak position of distribution can be inferred to be the z-axis position of sharp varying plane of X-ray absorption coefficients.

In the method of inferring the position of a sharp varying plane of X-ray absorption coefficients of the fourth viewpoint, data is sampled at multiple z-axis positions along at least two directions of different angles of the X-ray tube or detector relative to the object under test. The sampled data is accumulated in coordinate-correspondent buffers of respective xy coordinates on the X-ray trajectory. Next, the distribution along z-axis positions of accumulative values in the coordinate-correspondent buffers of the same xy coordinates is obtained, and the z-axis position of sharp varying plane of X-ray absorption coefficients relevant to the xy coordinates is inferred based on the distribution.

Accumulating data sampled along different directions in the buffers which correspond to coordinates on the X-ray trajectory produces values indicative of the X-ray absorption coefficients at the xy coordinates. An accumulative value at a portion with a large X-ray absorption coefficient differ greatly from an accumulative value at a portion with a small X-ray absorption coefficient. Accordingly, based on the distribution of accumulative values along z-axis positions in the coordinate-correspondent buffers for the same xy coordinates, the sharp-varying position of distribution can be inferred to be the z-axis position of sharp varying plane of X-ray absorption coefficients.

In the method of inferring the position of a sharp varying plane of X-ray absorption coefficients of the fifth viewpoint, data of detector channels at z-axis positions is stored in channel-correspondent buffers for respective detector channels. Next, the z-axis position of sharp varying plane of X-ray absorption coefficients for each detector channel is inferred based on the distribution along z-axis positions of the channel-correspondent buffers of the same detector channel. Next, the data of the inferred z-axis positions is stored in the coordinate-correspondent buffers of respective xy coordinates on the X-ray trajectory, data on the inferred z-axis position is sampled along at least one direction of the X-ray tube or detector different from the first-mentioned angle, and the sampled data is accumulated in the coordinate-correspondent correspondent buffers of respective xy coordinates on the X-ray trajectory. Based on the accumulative values in the coordinate-correspondent buffers, the xy-coordinate position of sharp varying plane of X-ray absorption coefficients for the inferred z-axis position is inferred.

An accumulative value at a portion with a large X-ray absorption coefficient differ greatly from an accumulative value at a portion with a small X-ray absorption coefficient. Accordingly, based on the distribution of accumulative values along z-axis positions in the coordinate-correspondent buffers for the same xy coordinates, the sharp-varying position of the distribution can be inferred to be the z-axis position of sharp varying plane of X-ray absorption coefficients. Next, adding the data obtained in different directions to the buffers which correspond to coordinates on the X-ray trajectory produces values indicative of the X-ray absorption coefficients at the xy coordinates. Accordingly, the xy coordinates of sharp varying plane of X-ray absorption coefficients can be inferred from the accumulative values.

In the X-ray CT apparatus of the sixth viewpoint, interpolation data on an image reconstruction plane is produced from data sampled by helical scanning based on the computation of weighted interpolation with weights that depend on the degree of the influence of partial volume on the interpolation data. Consequently, partial volume artifacts can be reduced.

In the X-ray CT apparatus of the seventh viewpoint, weighting factors are calculated based on the relation between the z-axis position of interpolation data, slice thickness and z-axis position of sharp varying plane of X-ray absorption coefficients. Consequently, weighting factors which depend on the degree of partial volume can be applied.

In the X-ray CT apparatus of the eighth viewpoint, X-ray attenuation coefficients on one and another sides of a sharp varying plane of X-ray absorption coefficients are evaluated based on data used for producing interpolation data. Next, a mean X-ray attenuation coefficient is evaluated by calculating a weighted mean of the two X-ray attenuation coefficients based on the weighting factors. Next, interpolation data is calculated by using the mean X-ray attenuation coefficient. The apparatus renders the weighting to the projection data, as will be explained in detail later, enabling information of smaller X-ray absorption coefficients to contribute significantly to the image.

The inventive interpolation data producing method is capable of producing interpolation data which is relieved of the influence of partial volume.

The inventive method of inferring the position of a sharp varying plane of X-ray absorption coefficients is capable of inferring the position of sharp varying plane of X-ray absorption coefficients.

The inventive X-ray CT apparatus is capable of carrying out properly the method of producing interpolation data and the method of inferring the position of a sharp varying plane of X-ray absorption coefficients.

These and other features and advantages of the present invention will become apparent from the following description of the preferred embodiments taken in conjunction with the accompanying drawings.

BRIEF DESCRIPTION OF THE DRAWINGS

FIG. 6 is a flowchart of the process of inferring the position of a sharp varying plane of X-ray absorption coefficients based on this embodiment;

DESCRIPTION OF THE PREFERRED EMBODIMENTS

Embodiment 1

Figure 1:
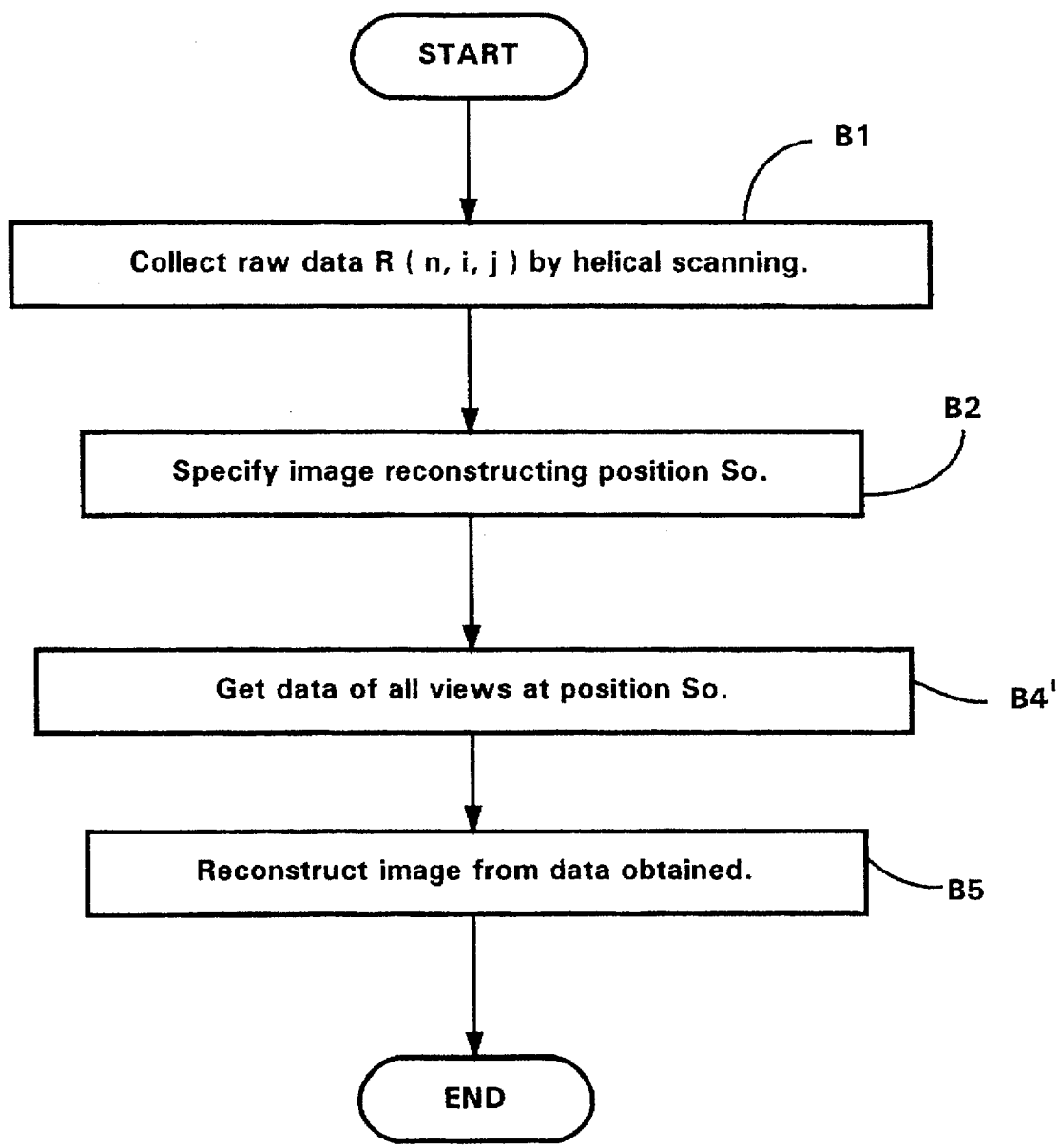
FIG. 1 is a flowchart showing a conventional sequential process for sampling raw data by helical scanning and forming an image from the data.
Figure 2:
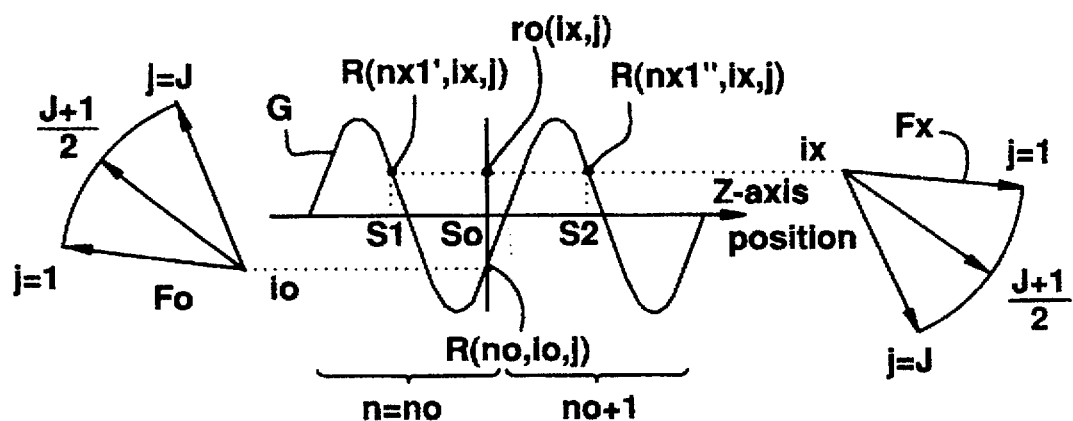
FIG. 2 is a diagram explaining a conventional interpolation data producing process.
Figure 3:
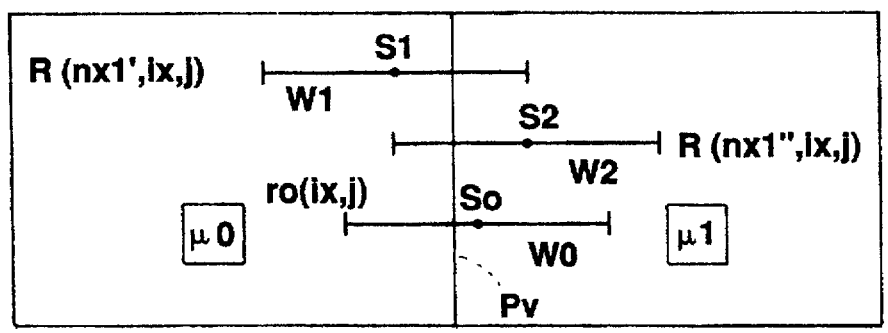
FIG. 3 is a diagram explaining the positional relation of raw data used for interpolation, the slice position of interpolation data and the position of sharp varying plane of X-ray absorption coefficients.
Figure 4A:
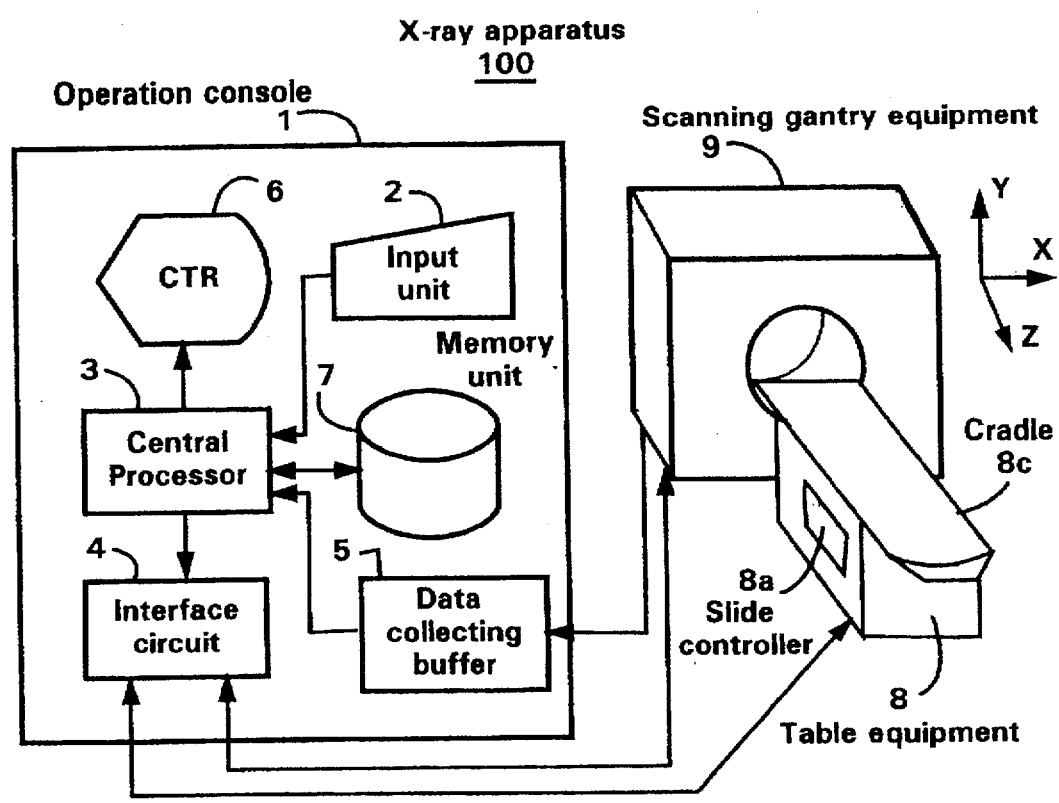
FIGS. 4A and 4B are diagrams showing the structure of the X-ray CT apparatus based on an embodiment of this invention.
Figure 4B:
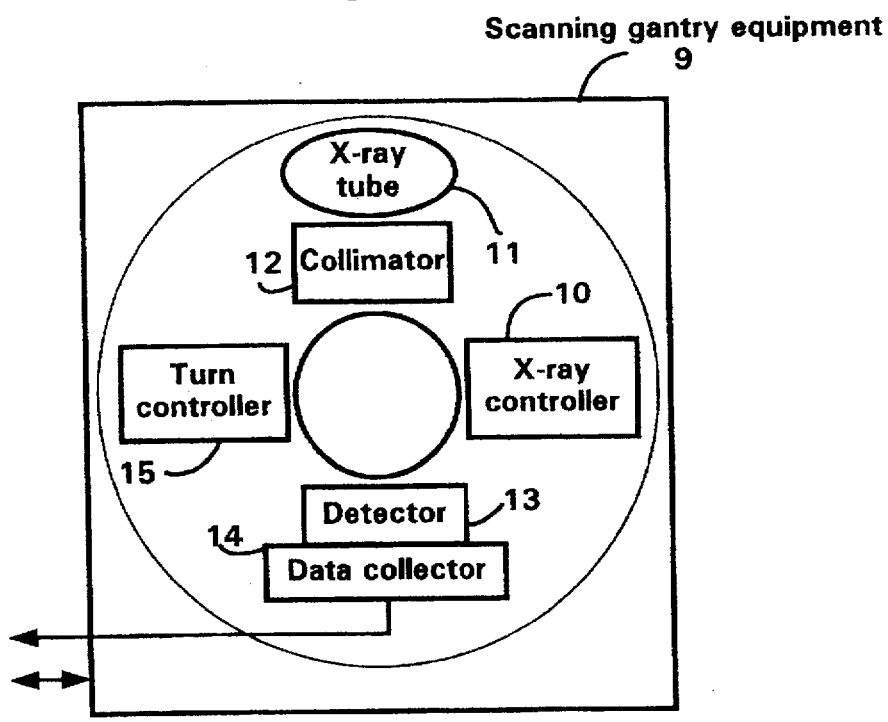

FIGS. 4A and 4B show the X-ray CT apparatus based on the first embodiment of this invention.

The X-ray CT apparatus 100 consists primarily of an operation console 1, a table equipment 8, and a scanning gantry equipment 9.

The operation console 1 includes an input unit 2 which receives operator's instructions and information, a central processor 3 which implements the scanning operation, the process of inferring the position of sharp varying plane of X-ray absorption coefficients, the process of producing interpolation data and the process of reconstructing an image, an interface circuit 4 which delivers control commands and signals to the table equipment 8 and scanning gantry equipment 9, a data sampling buffer circuit 5 which stores data sampled by the scanning gantry equipment 9, a CRT display unit 6 which displays images and data, and a memory unit 7 which stores programs and data.

The table equipment 8 including a slide controller 8a moves a cradle 8c, with an object under test (patient to be scanned) being placed thereon, in the z-axis direction.

The scanning gantry equipment 9 includes an X-ray controller 10, an X-ray tube 11, an collimator 12, a detector 13, a data collector 14, and a turn controller 15 which turns the X-ray tube 11 and associated devices around the longitudinal axis of the test object.

As an alternative arrangement, the scanning gantry equipment 9 may be moved in the z-axis direction in place of or in addition to the movement of the table equipment 8.

Figure 5:
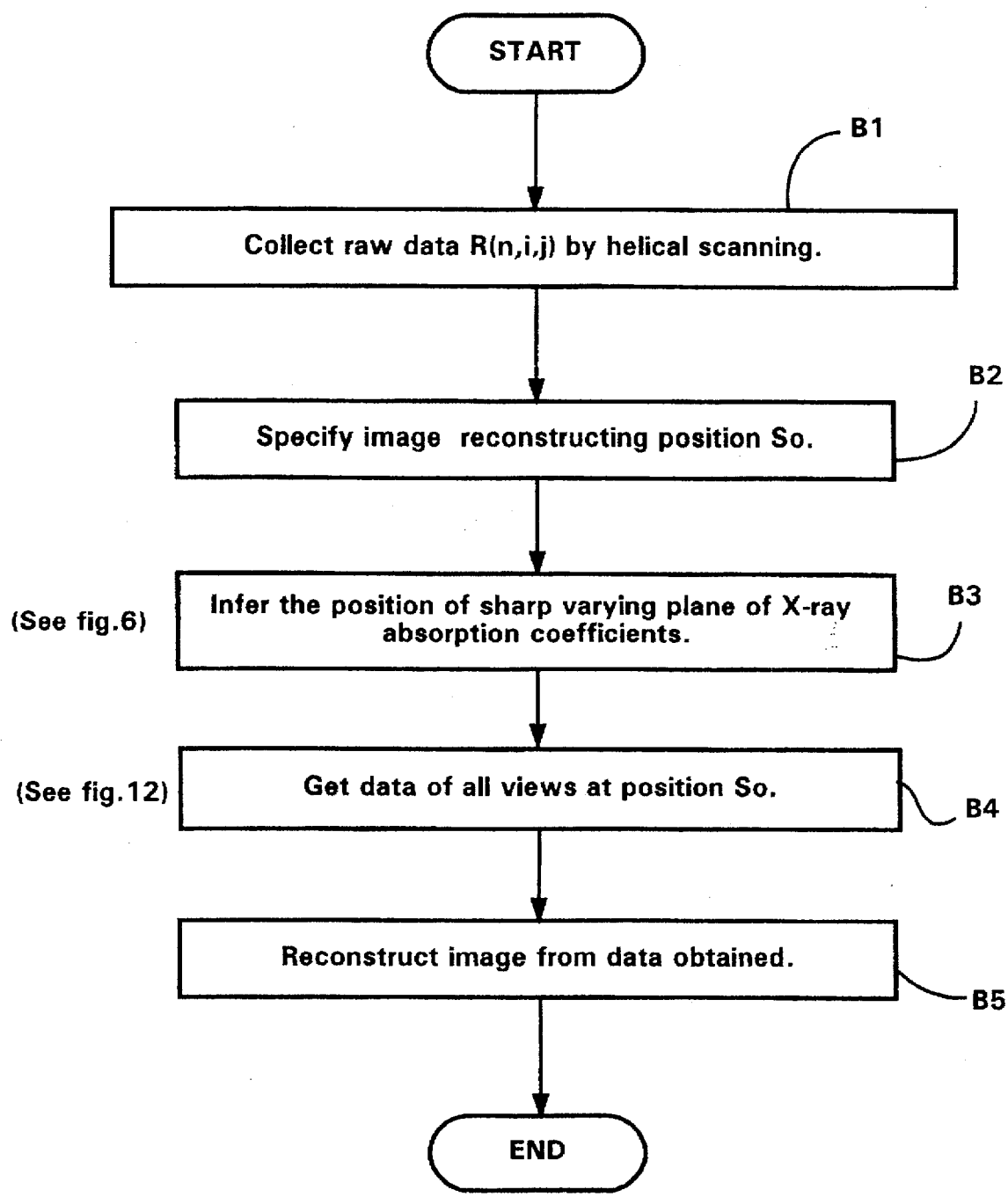
FIG. 5 is a flowchart of the process for collecting raw data by helical scanning and forming an image based on a first embodiment of the invention.

FIG. 5 shows by flowchart the sequential process of the X-ray controller 10 for collecting data by helical scanning and forming an image.

Step B1 samples raw data $R(n,i,j)$ by helical scanning. Specifically, with the X-ray tube 11, collimator 12 and detector 13 being operated to turn and the test object (or alternatively the X-ray tube 11, collimator 12 and detector 13) being moved straight along the z-axis, raw data $R(n,i,j)$ of multiple views is sampled at multiple sampling positions on the z-axis. Raw data is expressed in terms of the turn number n for the turning of the devices 11,12 and 13, view number i and detector channel number j, as mentioned previously.

Step B2 specifies an image reconstructing position So.

Step B3 infers the position (X,Y,Z) of a sharp varying plane of X-ray absorption coefficients, as will be explained later in connection with FIG. 6.

Step B4 samples data of all views at the position So needed for image reconstruction. Specifically, if raw data $R(no,io,j)$ of the position So exists, it is taken in, and furthermore data $ro(ix,j)$ for view number ix other than io is calculated by interpolation from raw data $R(nx',ix,j)$ of a nearby view with a smaller turn number than that of So (will be called "on one side" of So) and raw data $R(nx'',ix,j)$ of another nearby view with a larger turn number than that of So (will be called "on another side" of So). A weighting factor is calculated based on the relation of the z-axis position where the raw data is sampled, the slice thickness for the raw data and the z-axis position of sharp varying plane of X-ray absorption coefficients, and interpolation data is produced by the computation of interpolation with the weighting factor, as will be explained in detail later in connection with FIG. 12.

Step B5 converts the raw data $R(no,io,j)$ and interpolation data $to(ix,j)$ into projection data, and reconstructs the image of the position So from the projection data.

The step B4 occasionally calculates the interpolate data $ro(ix,j)$ from raw data $R(nt',it',jt')$ of a nearby confronting view on one side of So and raw data $R(nt'',it'',jt'')$ of another nearby confronting view on another side.

FIG. 6 shows by flowchart of PAD (Program Analysis Diagram) the process of inferring the position of sharp varying plane of X-ray absorption coefficients.

Figure 7:
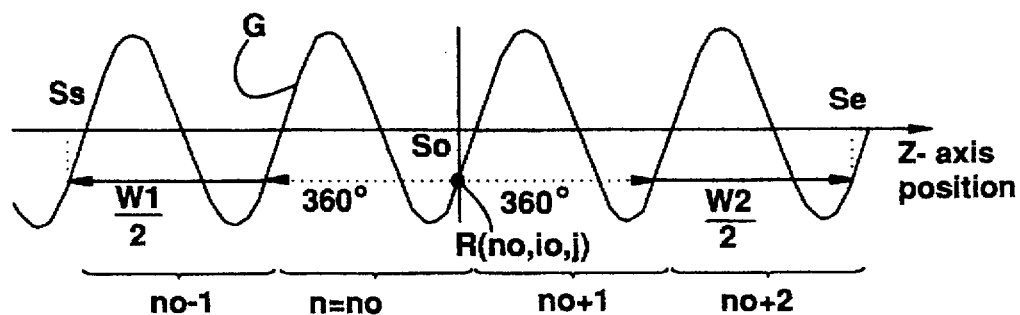
FIG. 7 is a diagram used to explain the start position and end position of the range of inference.

Step V1 sets a start position Ss and end position Se of the range of inference of the position of sharp varying plane of X-ray absorption coefficients. For example, in producing the interpolation data $to(ix,j)$, with the view angle range necessary for image reconstruction being 360°, based on the computation of interpolation using raw data $R(nx1',ix,j)$ of the same nearest view on one side of So and raw data $R(nx1'',ix,j)$ of the same nearest view on another side of So, the start position Ss is set to be a z-axis position with a distance of the width equivalent to 360° plus a half the slice thickness W1 on one side of So, and the end position Se is set to be a z-axis position with a distance of the width equivalent to 360° plus a half the slice thickness W2 on another side of So, as shown in FIG. 7. The range between Ss and Se may be set much wider. The width equivalent to 360° is generally comparable to the slice thickness.

Step V2 repeats the following step V3 by shifting the pointer Sm of the plane of concern from the start position Ss to the end position Se.

Step V3 repeats the following step V4 through step V6 by shifting the pointer Sk of difference evaluation from the position Sm to the position of 1-turn advancement.

Step V4 subtracts raw data $R(nk-1,ik,j)$ of the position of 1-turn precedence from raw data $R(nk,ik,j)$ of the position Sk thereby to evaluate the difference $d(nk,ik,j)$.

Figure 8:
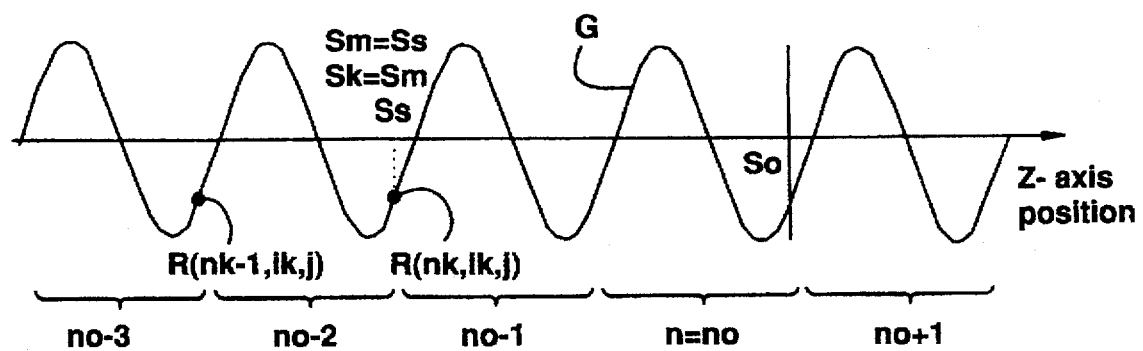
FIG. 8 is a diagram used to explain two pieces of raw data for which the difference is calculated.

FIG. 8 shows the raw data $R(nk,ik,j)$ of the position Sk and the $R(nk-1,ik,j)$ of the position of 1-turn precedence when Sm=Ss and Sk=Sm (i.e., Sm=Ss).

Step V5 tests as to whether the absolute value of difference $d(nk,ik,j)$ is greater than a threshold value α. If it is greater than α the sequence proceeds to step V6, or otherwise the sequence returns to step V3. The threshold value α is selected in advance such that the absolute value of difference $d(nk,ik,j)$ is greater than α when the sharp varying plane of X-ray absorption coefficients exists between the position Sk and the position of 1-turn precedence or the absolute value of difference $d(nk,ik,j)$ is smaller than α when it does not exist. Although the step V5 may be omitted, it prevents the accumulative value, which will be explained later, from increasing due to the accumulation of noises.

Step V6 adds the difference d(nk,ik,j) to the coordinate-correspondent buffer Bm(x,y) for the coordinates (x,y) on an X-ray trajectory T(ik,j) that is determined from the view number ik and detector channel number j.

Figure 9:
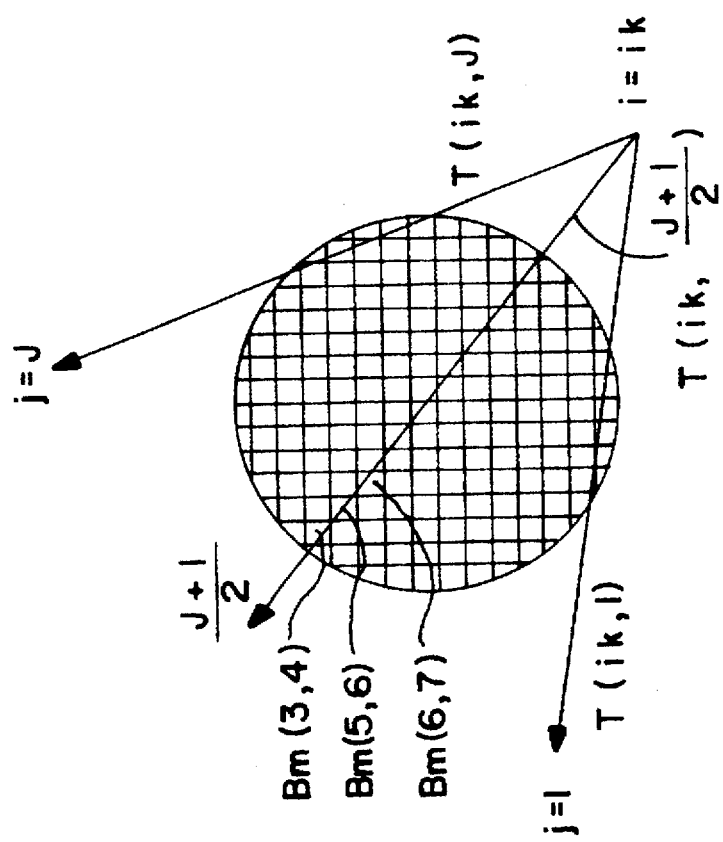
FIG. 9 is a conceptual diagram showing the X-ray trajectories and coordinate-correspondent buffers.

FIG. 9 shows X-ray trajectories T(ik,1), T(ik,(J+1)/2) and T(ik,J), and coordinate-correspondent buffers Bm(x,y).

For example, if the absolute value of the difference d(nk,ik,(j+1)/2) between raw data R(nk,ik,(J+1)/2) and raw data R(nk−1,ik,(j+1)/2) of the position of 1-turn precedence is greater than the threshold value α the difference d(nk,ik,(J+1)/2) is added to coordinate-correspondent buffers Bm(3, 4), Bm(5,6), Bm(7,8) and so on for coordinates (3,4), (5,6), (7,8) and so on located on the trajectory T(ik,(J+1)/2).

Figure 10:
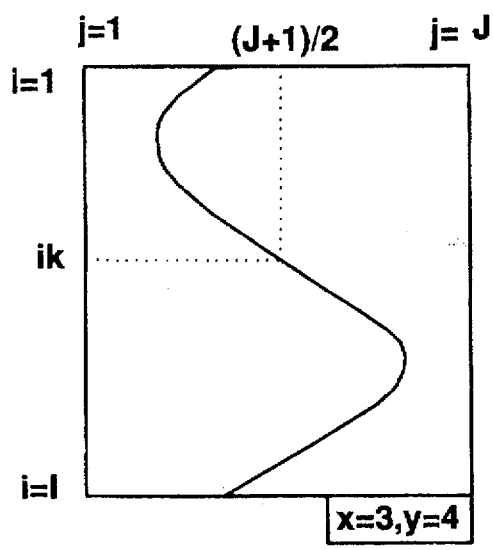
FIG. 10 is a diagram explaining the sinogram.

FIG. 10 shows the sinogram pertinent to coordinates (3,4). Using this sinogram reveals coordinates (x,y) located on an X-ray trajectory T(ik,j).

On completion of cycles of the steps V4–V6 as detected by the step V3, the coordinate-correspondent buffers Bm(x, y) contain accumulative values Dm(x,y) of the position Sm. Accumulative values Dm(x,y) are stored together with the position Sm. Since the nearer the position Sm to the sharp varying plane of X-ray absorption coefficients, the larger is the number of times of summation of the difference d(nk, ik,j) and thus the larger is the accumulative value Dm(x,y). The Dm(x,y) takes the maximum value when the position Sm coincides with the sharp varying plane of X-ray absorption coefficients.

On completion of cycles of the step V3 as detected by the step V2, accumulative values Dm(x,y) of all positions Sm from the start position Ss to the end position Se are stored.

During the loop of the step V3, using the previous accumulative value Dm' (x,y) simplifies the processing. Specifically, when Dm' (x,y) is d1+d2+ . . . +d10, then Dm(x,y) is d2+d3+ . . . +d10+d11, and accordingly Dm(x,y) is calculated simply by Dm' (x,y)dl+d11.

Returning to FIG. 6, step V7 repeats the following step V8 for all coordinates (x,y).

Step V8 finds for each coordinates (x,y) a position Sp among positions Sm at which the accumulative value Dm(x, y) is greater than the threshold value β and is the peak of distribution along positions Sm. If such position Sp is found, the coordinate (x,y) and position Sp are inferred to be the position of sharp varying plane of X-ray absorption coefficients.

Figure 11:
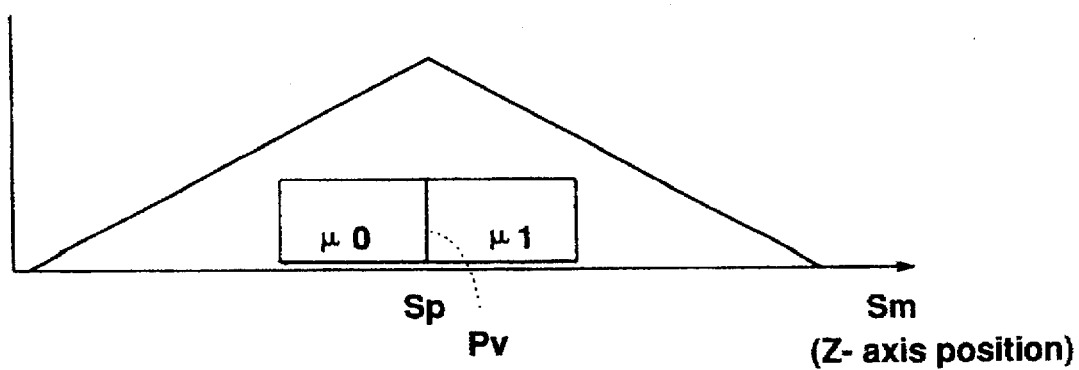
FIG. 11 is a diagram explaining the distribution of accumulative values.

FIG. 11 shows an example of the distribution of accumulative values Dm(3,4) along position Sm for xy coordinates (3,4).

It is inferred that there exists a sharp varying plane Pv of X-ray absorption coefficients at the position Sp where the distribution of Dm(3,4) has a peak. Accordingly, the position (X,Y,Z) of sharp varying plane Pv of X-ray absorption coefficients is determined to be (3,4,Sp).

Figure 12:
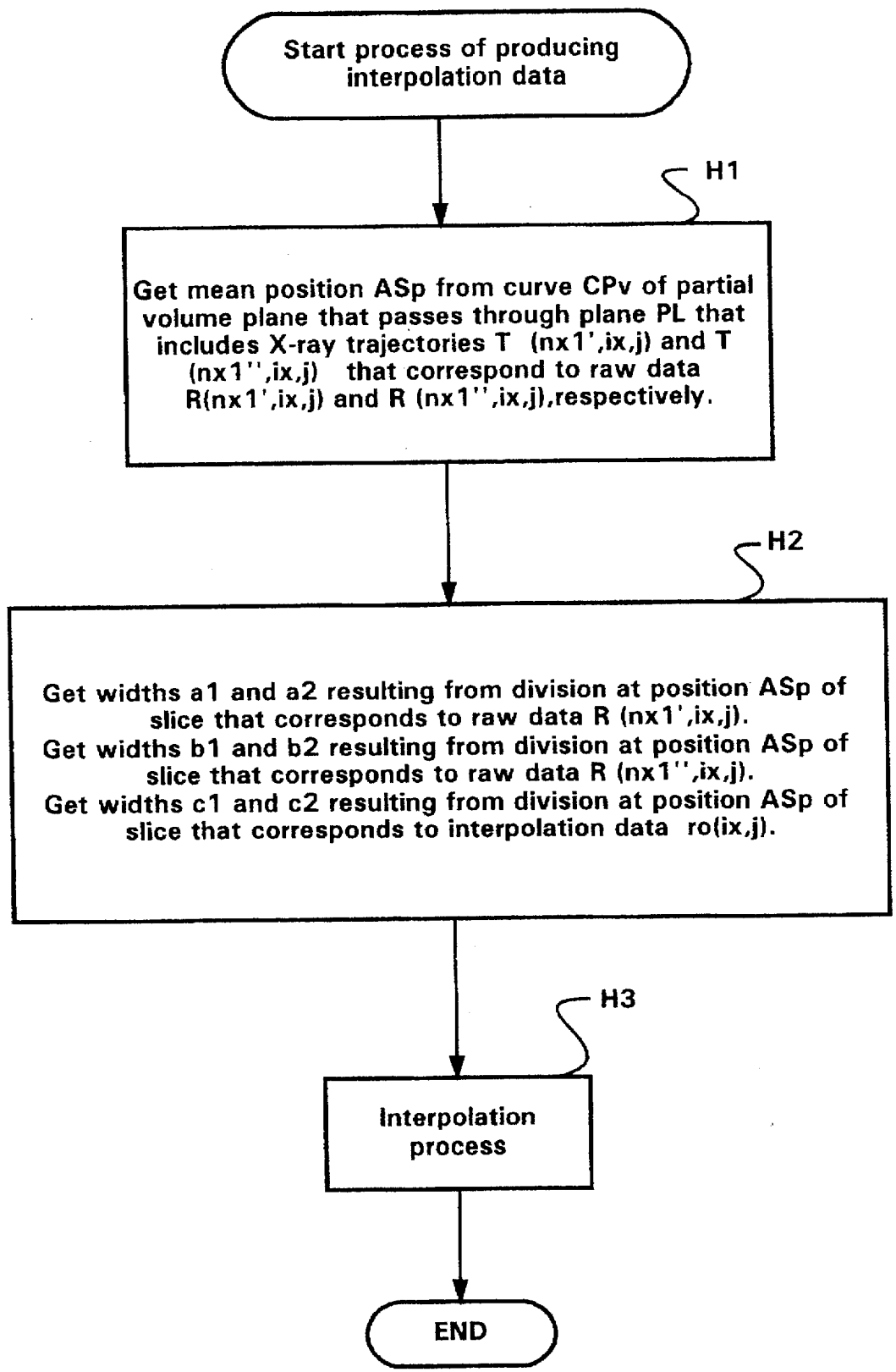
FIG. 12 is a flowchart of the interpolation data producing process.

FIG. 12 shows by flowchart the process of producing interpolation data.

Figure 13:
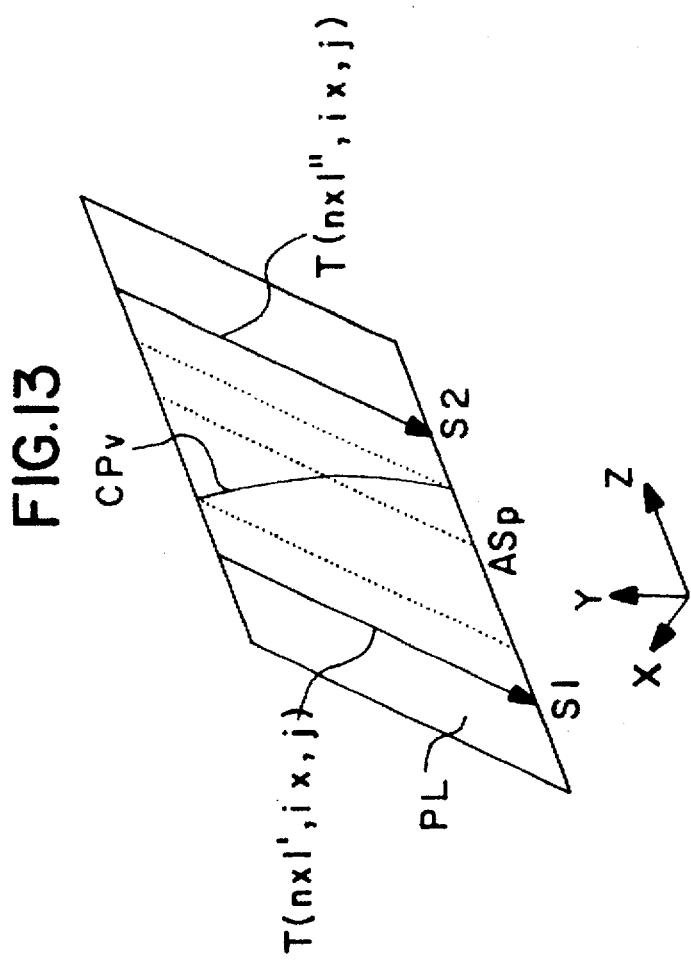
FIG. 13 is a diagram used to explain a mean position of sharp varying plane of X-ray absorption coefficients.

Step H1 evaluates a mean position ASp of sharp varying plane of X-ray absorption coefficients from a curve CPv of X-ray absorption coefficient sharp varying plane that passes through a plane PL that includes the X-ray trajectories T(nx1',ix,j) and T(nx1",ix,j) which correspond to the raw data R(nx1',ix,j) and R(nx1",ix,j), respectively, used for producing the interpolation data to(ix,j), as shown in FIG. 13. The ASp can be obtained as a z coordinate of the bisector of the curve CPv, for example.

Figure 14:
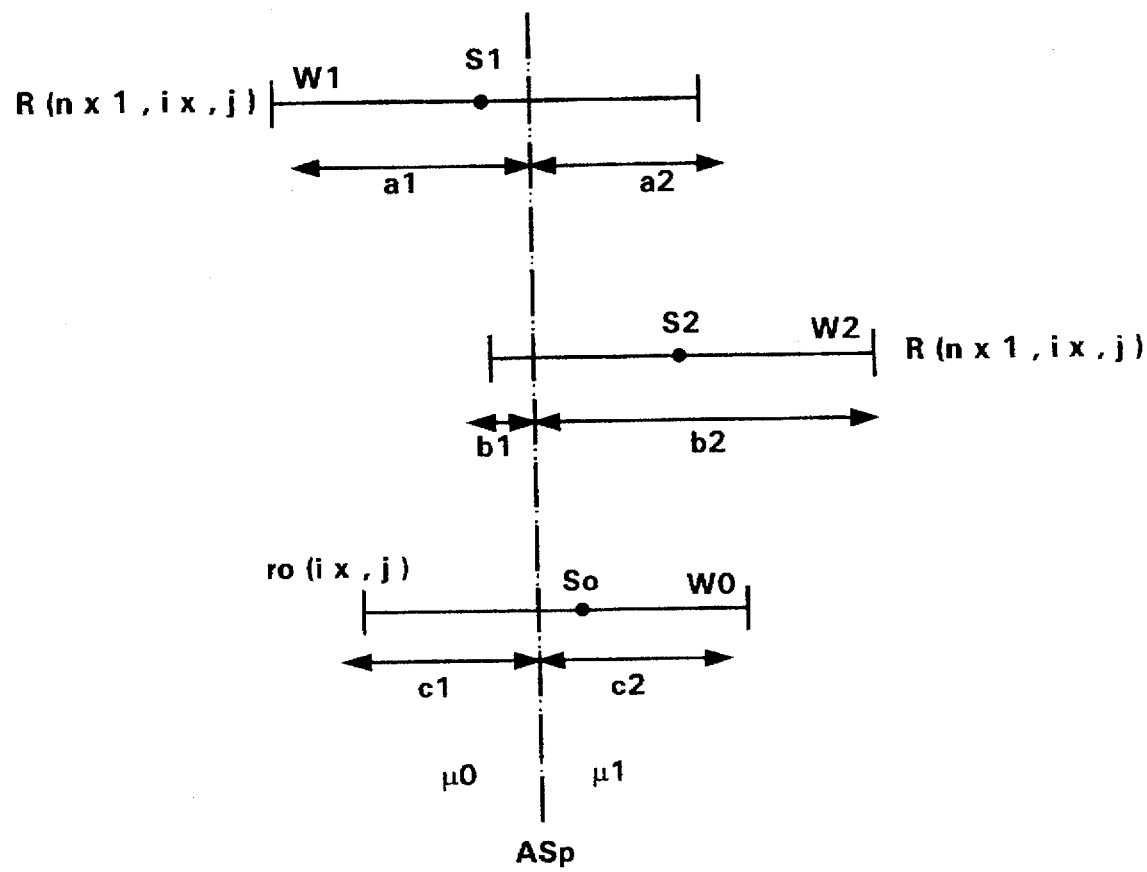
FIG. 14 is a diagram explaining the positional relation of raw data used for interpolation, slice position which corresponds to the interpolation data and mean position of sharp varying plane of X-ray absorption coefficients.

Step H2 evaluates widths a1 and a2 resulting from division of a slice thickness W1, which corresponds to the raw data R(nx1',ix,j), at the mean position ASp of X-ray absorption coefficient sharp varying plane, as shown in FIG. 14. Specifically, for a slice thickness W1 of "M", the widths a1 and a2 are as follows.

a1=0 if M/2+(Asp−S1) is negative, or a1=M if M/2+(Asp−S1) is greater than M, and a2=M−a1

Similarly, the step H2 evaluates widths b1 and b2 resulting from division of a slice thickness W2, which corresponds to the raw data R(nx1=,ix,j), at the mean position ASp of X-ray absorption coefficient sharp varying plane. Specifically, for a slice thickness W2 of "M", the widths b1 and b2 are as follows.

b1=0 if M/2+(Asp−S2) is negative, or b1=M if M/2+(Asp−S2) is greater than M, and b2=M−b1

Similarly, the step H2 evaluates widths c1 and c2 resulting from division of a slice thickness W0, which corresponds to the interpolation data ro(ix,j), at the mean position ASp of X-ray absorption coefficient sharp varying plane. Specifically, for a slice thickness W0 of "M", the widths c1 and c2 are as follows.

c1=0 if M/2+(Asp−So) is negative, or c1=M if M/2+(Asp−So) is greater than M, and c2=M−c1

Step H3 implements the computation of interpolation. Specifically, the following simultaneous equations (1) and (2) are solved to evaluate X-ray attenuation coefficients $K\mu0$ and $K\mu1$.

$$R(nx1',ix,j)=(a1/M) \exp\{-K\mu0\}+(a2/M) \exp\{-K\mu1\} \quad (1)$$

$$R(nx1'',ix,j)=(b1/M) \exp\{-K\mu0\}+(b2/M) \exp\{-K\mu1\} \quad (2)$$

Subsequently, the interpolation data to(ix,j) is evaluated based on the following formula.

$$ro(ix,j)=(c1/M) \exp\{-K\mu0\}+(c2/M) \exp\{-K\mu1\} \quad (3)$$

This interpolation data ro(ix,j) is calculated from the raw data R(nx1',ix,j) and R(nx1",ix,j) by weighted interpolation with the weighting factors a1/M, a2/M, b1/M, b2/M, c1/M and c1/M evaluated based on the relation of the z-axis position of slicing for the ro, slice thickness and z-axis position of sharp varying plane of X-ray absorption coefficients, and accordingly it comprehends the influence of partial volume appropriately, enabling the suppression of partial volume artifacts.

The following explains in brief the basis of the above formula (1).

For an incident X-ray strength Io, X-ray trajectory s and X-ray absorption coefficient $\mu(s)$, the transmitting X-ray strength I is expressed as follows.

$$I=Io \exp\{-\int\mu(s)ds\} \quad (4)$$

In FIG. 11, the incident X-ray strength at the portion a1 of the slice thickness W1 for the raw data R(nx1',ix,j) is (a1/M)Io and the X-ray absorption coefficient is $\mu0$, and therefore the transmitting X-ray strength Ia1 is given as follows.

$$Ia1=(a1/M) Io \exp\{-\int\mu0(s) ds\} \quad (5)$$

For the portion a2, the incident X-ray strength is (a2/M)Io and the X-ray absorption coefficient is $\mu1$, and therefore the transmitting X-ray strength Ia2 is given as follows.

$$Ia2=(a2/M) Io \exp\{-\int\mu1(s)ds\} \quad (6)$$

Accordingly, the total transmitting X-ray strength Ia detected is given as follows.

$$Ia = Ia1 + Ia2 \quad (7)$$
$$= (a1/M)Io \cdot \exp\{-\int\mu 0(s)ds\} + (a2/M)Io \cdot \exp\{-\int\mu 1(s)ds\}$$

Placing the $\int\mu 0(s)ds$ and $\int\mu (s)ds$ to be $K\mu 0$ and $K\mu 1$ gives:

$$Ia=(a1/M)\, Io \cdot \exp\{-K\mu 0\}+(a2/M)\, Io \cdot \exp\{-K\mu 1\} \quad (8)$$

The transmitting X-ray strength Ia gives the raw data R(nx1'ix,j), resulting in the formula (1)

The formulas (2) and (3) can be verified in the same manner.

Embodiment 2

The step H3 of the foregoing first embodiment can be altered to calculate the interpolation data as projection data.

Specifically, projection data Pr(ix,j) to be obtained is related to the interpolation data ro(ix,j) as follows.

$$Pr(ix,j)=\ln(ro(ix,j)) \quad (9)$$

It is analytically solved as follows.

$$Pr(ix,j) = -\ln(R(nxl',ix,j)) + \quad (10)$$
$$\ln(a1/M[\exp\{K(\mu 0-\mu 1)\}]^{b2/M} - a2/M[\exp\{K(\mu 0-\mu 1)\}]^{-a1/M})$$

or $$Pr(ix,j) = -\ln(R(nxl'',ix,j)) + \quad (11)$$
$$\ln(b1/M[\exp\{K(\mu 0-\mu 1)\}]^{b2/M} + b2/M[\exp\{K(\mu 0-\mu 1)\}]^{-b1/M})$$

In the above formulas (10) and (11), term $\exp\{(K(\mu 0-\mu 1)\}$ can be expressed as follows.

$$\exp\{K(\mu 0-\mu 1)\} = \quad (12)$$
$$\{-b2/M\exp(-\Delta P) + a2/M\}/\{b1/M\exp(-\Delta P) - a1/M\}$$

where $\Delta P$ signifies the following.

$$\Delta P = Pr(nxl',ix,j) - Pr(nxl'',ix,j) \quad (13)$$
$$= -\ln(R(nxl',ix,j)) + \ln(R(nxl'',ix,j))$$

In the preprocessing for the computation of interpolation by the formula (10) or (11), $\Delta P$ can be obtained from the known interpolation data R(nx1',ix,j) and R(nx1'',ix,j), and accordingly $\exp\{(K(\mu 0-\mu 1)\}$ can be obtained from the $\Delta P$.

The computation of interpolation of the formula (10) or (11) is carried out by using the $\exp\{K(\mu 0-\mu 1)\}$ obtained, thereby evaluating the interpolation data Pr(ix,j).

Embodiment 3

The step H3 of the foregoing first embodiment, in which the simultaneous equations (1) and (2) are solved, can be altered to evaluate the X-ray attenuation coefficients $K\mu 0$ and $K\mu 1$ in a different manner as follows.

Specifically, among raw data having the same view number and same detector channel number as those of the interpolation data ro(ix,j), raw data existing in the neighborhood of the position So on the side of decreasing turn numbers, e.g., three pieces of raw data R(nx1',ix,j), R(nx2',ix,j) and R(nx3',ix,j), are weight-averaged to evaluate mean raw data AvR', and the X-ray attenuation coefficient $K\mu 0$ is calculated based on AvR'=exp{(-K\mu 0)}.

Similarly, among raw data having the same view number and same detector channel number as those of the interpolation data to(ix,j), raw data existing in the neighborhood of the position So on the side of increasing turn numbers, e.g., three pieces of raw data R(nx1'',ix,j), R(nx2'',ix,j) and R(nx3'',ix,j), are weight-averaged to evaluate mean raw data AvR'', and the X-ray attenuation coefficient $K\mu 1$ is calculated based on AvR''=exp{(K\mu 1)}.

Embodiment 4

The step H3 of the foregoing first embodiment can be altered to obtain the interpolation data ro(ix,j) based on the following formula, instead of the formula (3).

$$ro(ix,j)=\exp\{-(c1/M)K\mu 0-(c2/M)K\mu 1\} \quad ((14)$$

Calculation of this formula is equivalently the evaluation of a mean X-ray absorption coefficient based on the weight-averaging of the X-ray attenuation coefficients $K\mu 0$ and $K\mu 1$ and the computation of interpolation data to(ix,j) by use of the resulting mean X-ray absorption coefficient.

The following explains in brief the basis of the above formula (14).

Figure 15:
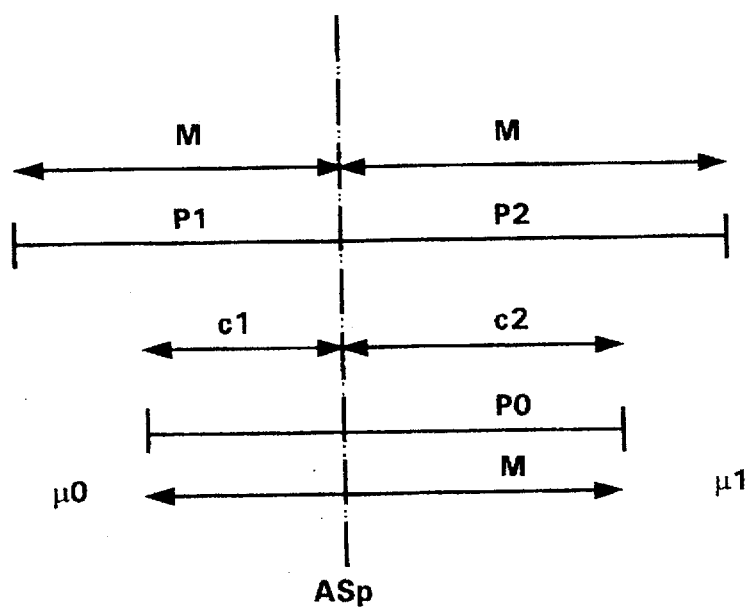
FIG. 15 is a diagram explaining the positional relation of the slice position which corresponds to projection data and mean position of sharp varying plane of X-ray absorption coefficients.

FIG. 15 shows projection data P1 of a slice with slice thickness M in a portion of X-ray coefficient $\mu 0$, projection data P2 of a slice with slice thickness M in a portion of X-ray absorption coefficient $\mu 1$, and projection data P0 of a slice having thickness c1 in a portion of X-ray absorption coefficient $\mu 0$ and thickness c2 in a portion of X-ray absorption coefficient $\mu 1$.

The projection data P0 is conceivably the sum of the projection data P1 multiplied by c1/M and the projection data P2 multiplied by c2/M as follows.

$$P0=(c1/M)P1+(c2/M)P2 \quad (15)$$

Assuming that the projection data P1 and P2 are derived from raw data R1 and R2, respectively, relations P1=-log{R1} and P2=-log{R2} hold.

The above formula (3) suggests the raw data R1 and R2 to be expressed as R1=exp{-K\mu 0} and R2=exp{-K\mu 1}. Then, P1=K\mu 0 and P2=K\mu 1.

Accordingly, the above formula (15) is reduced to the following formula.

$$P0=(c1/M)K\mu 0+(c2/M)K\mu 1 \quad (16)$$

Assuming that the projection data P0 is derived from raw data R0, it is expressed as P0=-log{R0}, which is converted into an inverse function of R0=exp{-P0}.

Substituting the above formula (11) into this function gives:

$$R0=\exp\{-(c1/M)K\mu 0-(c2/M)K\mu 1\} \quad (17)$$

This formula (17) for the raw data R0 is consistent with the above formula (11) for the interpolation data ro.

Embodiment 5

The fifth embodiment of this invention is a method of inferring the position of a sharp varying plane of X-ray absorption coefficients without being based on helical scanning.

Figure 16:
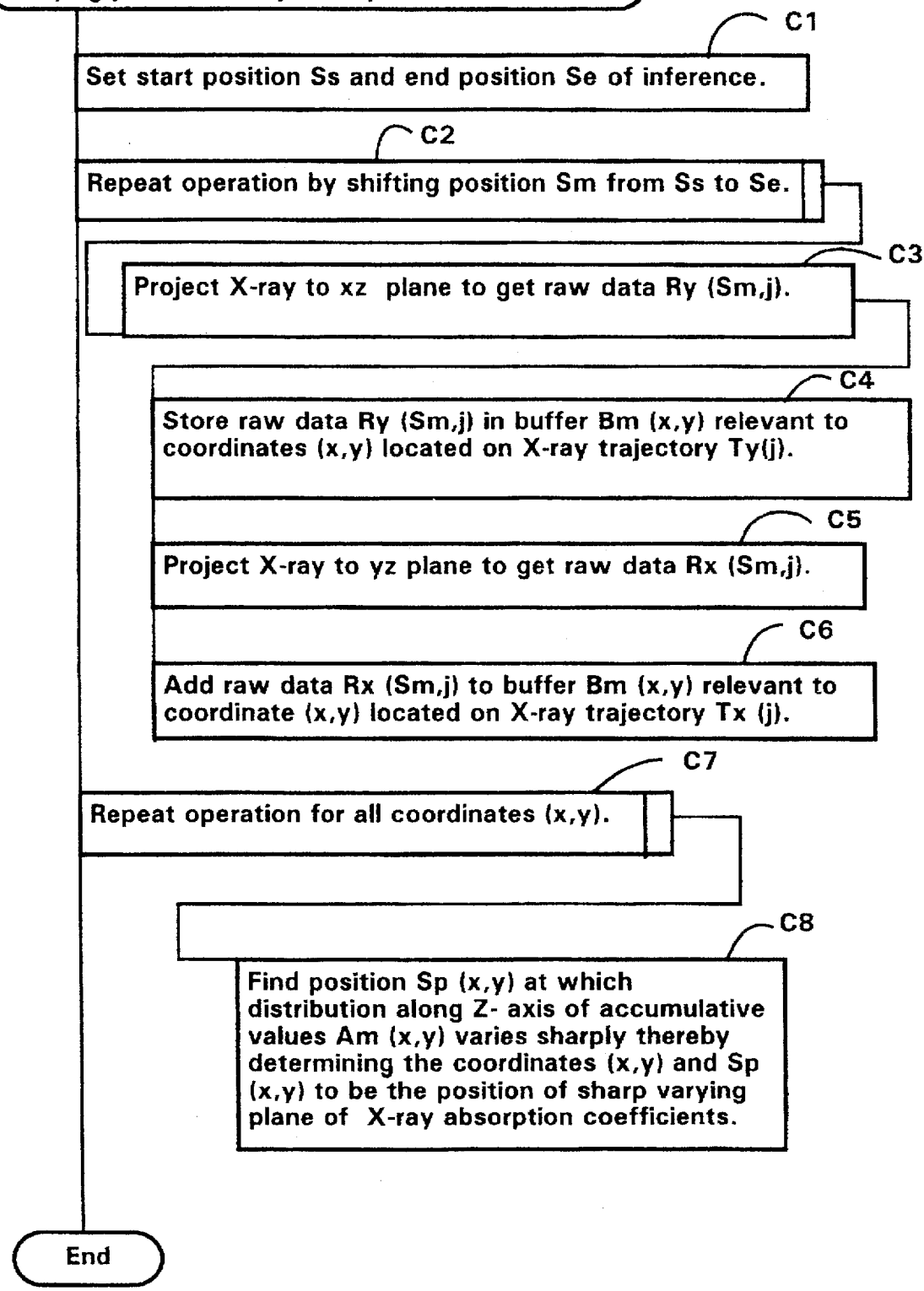
FIG. 16 is a flowchart of the process of inferring the position of a sharp varying plane of X-ray absorption coefficients based on a third embodiment of the invention.

FIG. 16 shows by flowchart (PAD) the process of inferring the position of sharp varying plane of X-ray absorption coefficients.

Step C1 sets a start position Ss and end position Se of the range of inference of the position of sharp varying plane of X-ray absorption coefficients.

Step C2 repeats the following steps C3 through C6 by shifting the scanning position pointer Sm from the start position Ss to the end position Se.

Step C3 places the X-ray tube 11, collimator 12 and detector 13 at their angular positions so that the X-ray is projected to the xz plane, and samples raw data Ry(Sm,j) at the scanning position Sm.

Figure 17:
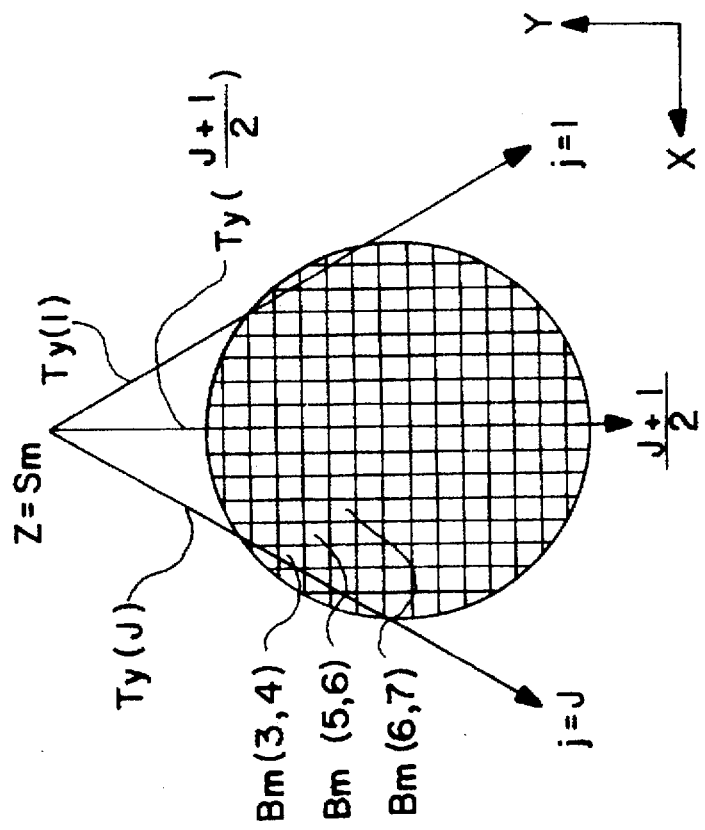
FIG. 17 is a conceptual diagram of X-ray trajectories and coordinate-correspondent buffers.

Step C4 stores the raw data Ry(Sm,j) in the coordinate-correspondent buffer Bm(x,y) relevant to the coordinate (x,y) located on the X-ray trajectory Ty(j) which is determined by the detector channel number j, as shown in FIG. 17.

Step C5 relocates the X-ray tube 11, collimator 12 and detector 13 so that the X-ray is projected to the yz plane, and samples raw data Rx(Sm,j) at the sampling position Sm.

Figure 18:
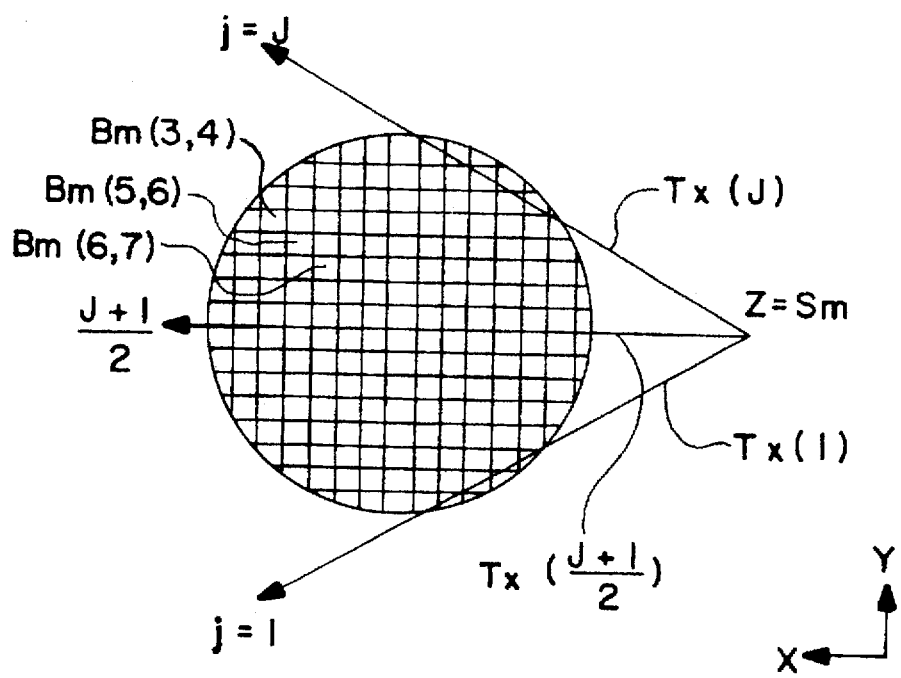
FIG. 18 is another conceptual diagram of X-ray trajectories and coordinate-correspondent buffers.

Step C6 adds the raw data Rx(Sm, j) to the buffer Bm(x,y) relevant to the coordinate (x,y) located on the X-ray trajectory Tx(j) which is determined by the detector channel number j, as shown in FIG. 18.

On completion of cycles of the steps C3–C6 as detected by the step C2, the coordinate-correspondent buffers Bm(x,y) contain accumulative values Am(x,y) of the positions Sm ranging from Ss to Se.

Step C7 repeats the following step C8 for all coordinates (x,y).

Step C8 finds for individual coordinates (x,y) a position Sp at which the distribution along the z-axis of the accumulative values Am(x,y) in the buffers Bm(x,y) varies sharply. If such position Sp is found, the coordinate (x,y) and position Sp are inferred to be the position of sharp varying plane of X-ray absorption coefficients.

Figure 19:
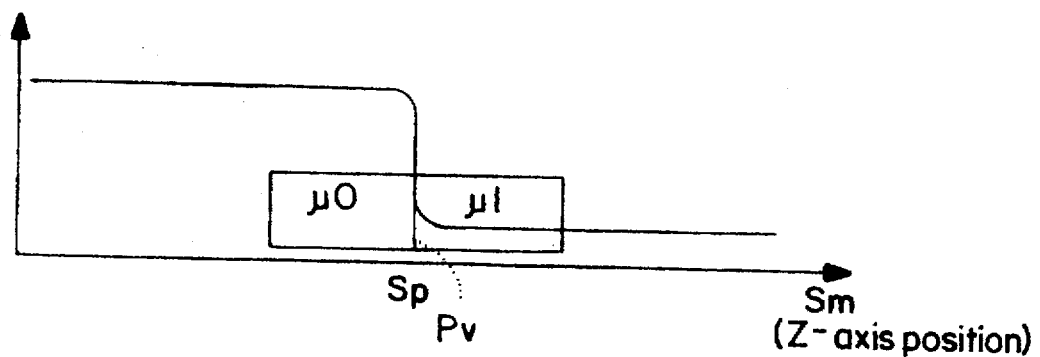
FIG. 19 is a diagram used to explain the distribution of accumulative values.

FIG. 19 shows an example of the distribution of accumulative values Am(3,4) along positions Sm for xy coordinates (3,4).

It is inferred that there exists a sharp varying plane Pv of X-ray absorption coefficients at the position Sp where the distribution of Am(3,4) varies sharply. Accordingly, the position (X,Y,Z) of sharp varying plane Pv of X-ray absorption coefficients is determined to be (3,4,Sp).

Although in this embodiment the position of sharp varying plane Pv of X-ray absorption coefficients is inferred from raw data Rx(Sm,j) and Ry(Sm,j) sampled by X-ray projection in two intersecting directions, the accuracy of inference is enhanced by adding raw data sampled by X-ray projection in more other directions.

Embodiment 6

The sixth embodiment of this invention is another method of inferring the position of a sharp varying plane of X-ray absorption coefficients without being based on helical scanning.

Figure 20:
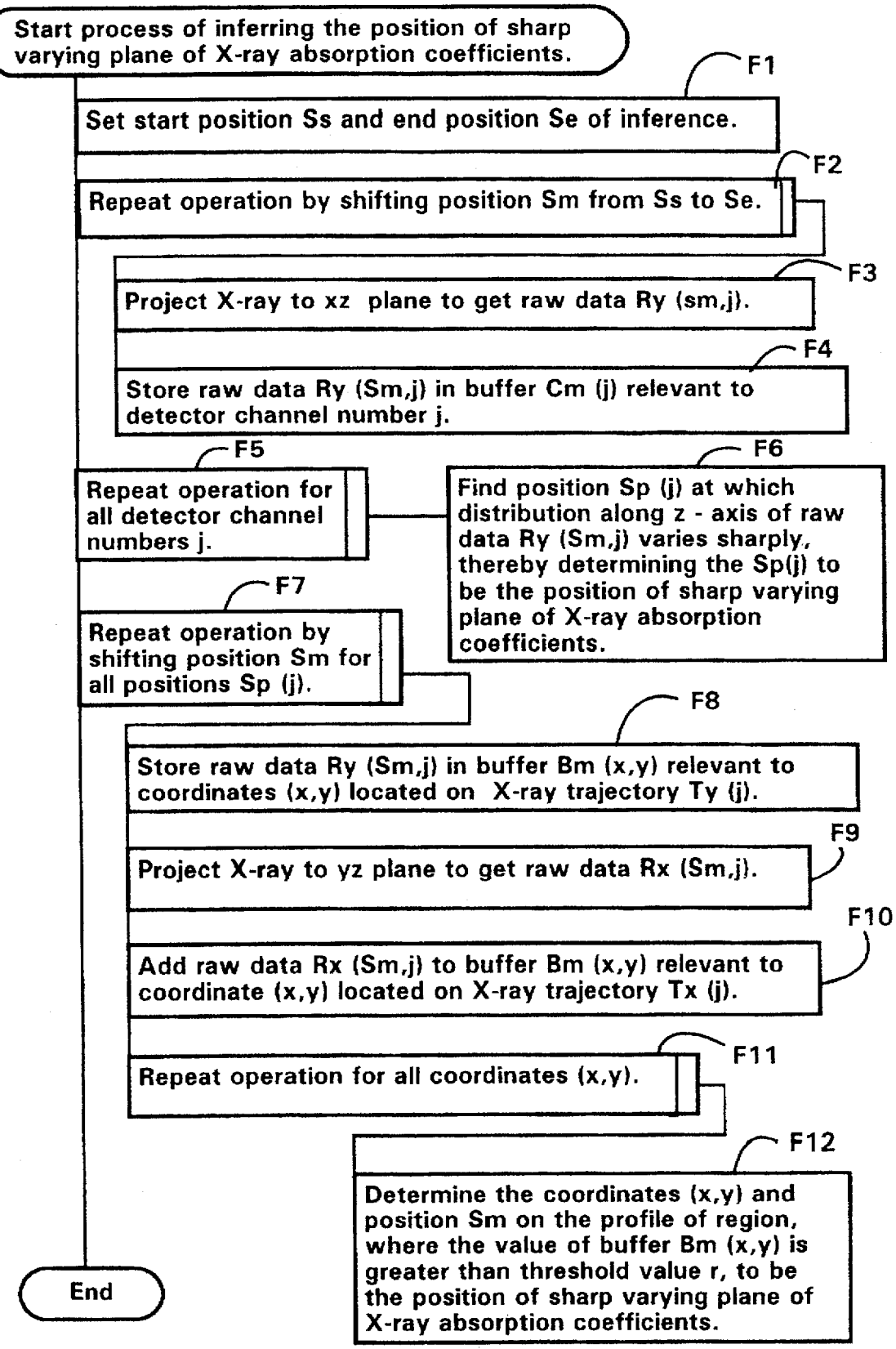
FIG. 20 is a flowchart of the process of inferring the position of a sharp varying plane of X-ray absorption coefficients based on a fourth embodiment of the invention.

FIG. 20 shows by flowchart the process of inferring the position of sharp varying plane of X-ray absorption coefficients.

Step F1 sets a start position Ss and end position Se of the range of inference of the position of sharp varying plane of X-ray absorption coefficients.

Step F2 repeats the following steps F3 and F4 by shifting the scanning position pointer Sm from the start position Ss to the end position Se.

Step F3 places the X-ray tube 11, collimator 12 and detector 13 at their angular positions so that the X-ray is projected to the xz plane, and samples raw data Ry(Sm,j) at the scanning position Sm.

Step F4 stores the raw data Ry(Sm,j) in the channel-correspondent buffer Cm(j) relevant to the detector channel number j.

On completion of cycles of the steps F3 and F4 as detected by the step F2, the channel-correspondent buffers Cm(j) contain raw data Ry(Sm,j) of the positions Sm ranging from Ss to Se.

Step F5 repeats the following step F6 for all channel numbers j.

Step F6 finds for individual channel number j a position Sp(j) at which the distribution of raw data Ry(Sm,j) along the z-axis varies sharply. Such position Sp(j) is inferred to be the position of sharp varying plane of X-ray absorption coefficients.

On completion of cycles of the step F6 as detected by the step F5, positions Sp(j) of sharp varying plane of X-ray absorption coefficients for all detector channel numbers j are detected.

Step F7 repeats the following steps F8 through F11 by setting the position Sp(j) sequentially in the scanning position counter Sm.

Step F8 stores the raw data Ry(Sm,j) in the coordinate-correspondent buffer Bm(x,y) relevant to the coordinate (x,y) on the X-ray trajectory Ty(j) which is determined by the detector channel number j.

Step F9 projects the X-ray onto the yz plane at the scanning position Sm, and samples raw data Rx(Sm,j).

Step F10 adds the raw data Rx(Sm,j) to the coordinate-correspondent buffer Bm(x,y) relevant to the coordinates (x,y) on the X-ray trajectory Tx(j) which is determined by the detector channel number j.

Step F11 repeats the following step F12 for all coordinates (x,y).

Step F12 tests for individual coordinates (x,y) as to whether or not the contents of buffer Bm(x,y) is greater than a threshold value γ. It obtains the profile of the range of values of buffers Bm(x,y) in excess of the threshold value γ, and infers from the coordinates (x,y) of profile and positions Sm that the position (x,y,Sm) is the position of sharp varying plane of X-ray absorption coefficients.

Variant embodiments

Instead of using projection data R(nx',ix,j) and R(nx",ix,j) of the same view number and same detector channel number as those of interpolation data to(ix,j) in the foregoing first through sixth embodiments, projection data R(nt',it',jt') and R(nt",it",jt") of the confronting view against the interpolation data ro(ix,j) may be used.

Many widely different embodiments of the invention may be constructed without departing from the spirit and scope of the present invention. It should be understood that the present invention is not limited to the specific embodiments described in the specification, except as defined in the appended claims.

What is claimed is:

1. A method of producing interpolation data comprising the steps of:

collecting data while turning at least-ray of an X-ray tube and a detector around an object under test and providing a linear movement for said object relative to said X-ray tube and/or detector;

calculating weights that depend on the degree of the influence of partial volume on data at an interpolation position; and producing interpolation data for an image reconstruction plane from the collected data based on computation of weighted interpolation with the weights.

2. A method of producing interpolation data according to claim 1, wherein said method evaluates X-ray attenuation coefficients on both sides of a sharp varying plane of X-ray absorption coefficients from data used for producing the interpolation data, calculates a mean X-ray attenuation coefficient by weight-averaging the X-ray attenuation coefficients with said weights, and calculates interpolation data by using the mean X-ray attenuation coefficient.

3. A method of producing interpolation data according to claim 1, wherein said computation of weighted interpolation is implemented so that the interpolation data is produced as projection data.

4. A method of inferring the position of a sharp varying plane of X-ray absorption coefficients, said method comprising the steps of:

collecting data while turning at least one of an X-ray tube and a detector around an object under test and providing a linear movement for said object relative to said X-ray tube and/or detector;

calculating the difference of two pieces of data having a same X-ray trajectory and existing on both sides of a plane of concern, and accumulating the difference values in a coordinate-correspondent buffer of respective xy coordinates on the X-ray trajectory, said calculating and accumulating being repeated for data of multiple views near the plane of concern;

storing the accumulated values in said buffers together with the z-axis position of the plane of concern, said storing being repeated while varying the z-axis position within a prescribed range on the plane of concern;

obtaining the distribution along z-axis positions of the accumulated values in said buffers of same xy coordinates; and inferring the z-axis position of sharp varying plane of X-ray absorption coefficients for the xy coordinates based on the distribution.

5. A method of inferring the position of a sharp varying plane of X-ray absorption coefficients, said method comprising the steps of:

sampling data at multiple z-axis positions along at least two directions of different angles of an X-ray tube or a detector relative to an object under test;

accumulating the sampled data in coordinate-correspondent buffers of respective xy coordinates on the X-ray trajectories;

obtaining the distribution along z-axis positions of the accumulated values in said buffers of same xy coordinates; and inferring the z-axis position of sharp varying plane of X-ray absorption coefficients for the xy coordinates based on the distribution.

6. A method of inferring the position of a sharp varying plane of X-ray absorption coefficients, said method comprising the steps of:

sampling data at multiple z-axis positions along a first direction of an X-ray tube or a detector relative to an object under test;

storing sampled data of respective detector channels at respective z-axis positions in channel-correspondent buffers of respective detector channels;

obtaining the distribution along z-axis positions of contents of said buffers of a same detector channel;

inferring the z-axis position of sharp varying plane of X-ray absorption coefficients for respective detector channels based on the distribution;

storing data of the inferred z-axis positions in coordinate-correspondent buffers of respective xy coordinates on the X-ray trajectories;

sampling data at the inferred z-axis positions along at least one direction of said X-ray tube or detector different from the first direction;

accumulating the sampled data in the coordinate-correspondent buffers for respective xy coordinates on the X-ray trajectories; and inferring the xy-coordinate position of sharp varying plane of X-ray absorption coefficients for the inferred z-axis position based on the accumulated values in the coordinate-correspondent buffers.

7. An X-ray CT apparatus comprising:

means for collecting data while turning at least one of an X-ray tube and a detector around an object under test and providing a linear movement for said object relative to said X-ray tube and/or detector;

means for calculating weighting factors that depend on the degree of the influence of partial volume on data at an interpolation position;

means for computing weighted interpolation data based on the calculated weighting factors for the data collected by said data collecting means; and means for reconstructing an image on an image reconstruction plane by implementing image reconstructing computation by using the weighted interpolation data on the image reconstruction plane resulting from the weighted interpolation by said weighted interpolation computing means.

8. An X-ray CT apparatus according to claim 7, wherein said weighting factor calculating means calculates weighting factors based on the relation between the z-axis position of interpolation data, slice thickness and z-axis position of sharp varying plane of X-ray absorption coefficients.

9. An X-ray CT apparatus according to claim 7 or 8, wherein said weighted interpolation computing means calculates X-ray attenuation coefficients on both sides of a sharp varying plane of X-ray absorption coefficients based on data used for producing weighted interpolation data, evaluates a mean X-ray attenuation coefficient by calculating a weighted mean of X-ray attenuation coefficients based on the weighting factors, and calculates the weighted interpolation data by using the mean X-ray attenuation coefficient.

10. An X-ray CT apparatus according to claim 7 or 8, wherein said weighted interpolation computing means implements the computation of weighted interpolation so that the weighted interpolation data is produced as projection data.

* * * * *